(12) United States Patent
Morgan et al.

(10) Patent No.: US 6,923,824 B2
(45) Date of Patent: Aug. 2, 2005

(54) APPARATUS AND METHOD FOR SECURING SUTURE TO BONE

(75) Inventors: Daniel E. Morgan, Salem, MA (US); Paul V. Fenton, Jr., Marblehead, MA (US); Thomas N. Fenton, Ipswich, MA (US); Vincent P. Novak, Groton, MA (US)

(73) Assignee: Axya Medical, Inc., Beverly, MA (US)

( * ) Notice: Subject to any disclaimer, the term of this patent is extended or adjusted under 35 U.S.C. 154(b) by 0 days.

(21) Appl. No.: 09/952,279

(22) Filed: Sep. 12, 2001

(65) Prior Publication Data

US 2002/0052629 A1 May 2, 2002

Related U.S. Application Data (60) Provisional application No. 60/231,859, filed on Sep. 12, 2000.

(51) Int. Cl.$^7$ ................................................ A61B 17/04
(52) U.S. Cl. ..................................................... 606/232
(58) Field of Search ............................ 606/72, 73, 232, 606/75

(56) References Cited

U.S. PATENT DOCUMENTS

| | | | |
|---|---|---|---|
| 3,513,848 A | * | 5/1970 | Garvey et al. ............... 606/228 |
| 4,632,100 A | | 12/1986 | Somers et al. |
| 4,673,323 A | * | 6/1987 | Russo .......................... 411/107 |
| 5,102,421 A | * | 4/1992 | Anspach, Jr. ................ 606/232 |
| 5,152,790 A | | 10/1992 | Rosenberg et al. |
| 5,156,616 A | | 10/1992 | Meadows et al. |
| 5,370,662 A | * | 12/1994 | Stone et al. .................. 606/232 |
| 5,443,482 A | * | 8/1995 | Stone et al. .................. 606/232 |
| 5,534,011 A | * | 7/1996 | Greene et al. ............... 606/232 |
| 5,683,419 A | | 11/1997 | Thal |
| 5,702,397 A | * | 12/1997 | Goble et al. ................... 606/72 |
| 5,868,789 A | * | 2/1999 | Huebner ...................... 606/232 |
| 5,899,920 A | | 5/1999 | DeSatnick et al. |
| 5,964,783 A | * | 10/1999 | Grafton et al. .............. 606/232 |
| 6,045,574 A | * | 4/2000 | Thal ............................ 606/232 |
| 6,056,751 A | * | 5/2000 | Fenton, Jr. .................... 606/72 |
| 6,143,017 A | * | 11/2000 | Thal ............................ 606/232 |
| 6,203,572 B1 | * | 3/2001 | Johnson et al. ........... 623/13.15 |
| 6,436,124 B1 | * | 8/2002 | Anderson et al. ............ 606/232 |
| 6,527,795 B1 | * | 3/2003 | Lizardi ........................ 606/232 |

* cited by examiner

*Primary Examiner*—Gary Jackson
(74) *Attorney, Agent, or Firm*—McDermott Will & Emery LLP (57) ABSTRACT

A suture anchor for securing soft tissue to bone, including a body and a continuous suture loop. The body extends along a longitudinal axis between opposing first and second ends, and has an external threaded portion extending coaxial with the axis, and a bore extending from the second end towards the first end. The continuous suture loop is secured within the bore of the body so that at least a portion of the loop extends from the second end of the body to form an eyelet.

25 Claims, 10 Drawing Sheets

APPARATUS AND METHOD FOR SECURING SUTURE TO BONE

CROSS-REFERENCE TO RELATED APPLICATIONS

The present application claims priority to provisional U.S. patent application Ser. No. 60/231,859, filed on Sep. 12, 2000, which is assigned to the assignee of the present application and incorporated herein by reference.

FIELD OF THE INVENTION

The present invention generally relates an apparatus and method for securing suture to bone, and more particularly, to suture anchors for securing soft tissue to bone.

BACKGROUND OF THE INVENTION

When soft tissue tears away from bone, reattachment becomes necessary. Various devices, including sutures alone, screws, staples, wedges, and plugs have been used in the past to secure soft tissue to bone.

Recently, various types of threaded suture anchors have been developed for this purpose. Some threaded suture anchors are designed to be inserted into a pre-drilled hole. Other suture anchors are self-tapping.

U.S. Pat. No. 4,632,100 discloses a cylindrical threaded suture anchor. The suture anchor of the '100 patent includes a drill bit at a leading end for boring a hole in a bone, followed by a flight of threads spaced from the drill bit for securing the anchor into the hole created by the drill bit. U.S. Pat. No. 5,370,662 discloses a suture anchor having a flight of threads which extend to the tip of the anchor. U.S. Pat. No. 5,156,616 discloses a similar suture anchor having an axial opening for holding a knotted piece of suture.

All of the above-noted suture anchors include structure for attaching the suture to the anchor. U.S. Pat. No. 4,632,100, for example, discloses and claims a press-fitted disc and knot structure which secures the suture to the anchor. In other suture anchors, such as those disclosed in U.S. Pat. No. 5,370,662, the suture is passed through an eyelet located on the proximal end of the anchor. U.S. Pat. No. 5,152,790 discloses a suture anchor with a rotatable ring for securing suture to the suture anchor.

The devices discussed above are fairly time consuming and complicated to fasten the soft tissue against the bone mass. It is also difficult for these devices to keep the soft tissue tightly attached to the bone mass during the body's healing process.

It would therefore be an advantage to provide a suture anchor that simplifies the operation process and effectively secures the soft tissue against the bone mass during the body's healing period. Preferably, the suture anchor will be provided with an eyelet that is movable with respect to the anchor in order to simplify the process of attaching a suture to the eyelet.

SUMMARY OF THE INVENTION

In response, the present invention provides a suture anchor for securing soft tissue to bone, including a body and a continuous suture loop. The body extends along a longitudinal axis between opposing first and second ends, and has an external threaded portion extending coaxial with the axis, and a bore extending from the second end towards the first end. The continuous suture loop is secured within the bore of the body so that at least a portion of the loop extends from the second end of the body to form an eyelet.

The continuous suture loop of the anchor provides strength and a flexible eyelet, which can ease the process of threading a suture through the eyelet during a surgical procedure. According to one aspect of the present invention, at least a portion of an outer surface of the continuous suture loop is bonded to an inner surface of the bore of the body.

According to another aspect, the suture loop is secured in the bore by a retainer secured to the body and extending through the loop generally laterally with respect to the axis. According to an additional aspect, the loop is movable between the body and the retainer. According to a further aspect, the retainer is unitary with the body. In one aspect, the body and the retainer are formed about the suture loop from at least two longitudinal portions bonded together around the suture loop.

According to a further aspect, the body includes a second bore extending generally laterally with respect to the axis, the retainer is received in the second bore, and at least a portion of an outer surface of the retainer is secured to an inner surface of the second bore. According to an additional aspect, at least a portion of an outer surface of the retainer is ultrasonically bonded to an inner surface of the second bore.

In one embodiment, the anchor further includes a pulley supporting the suture loop on the retainer. Preferably, the pulley is rotatably mounted on the retainer.

According to an additional aspect, the longitudinal bore extends between the first and the second ends of the body and the retainer is wedged within an inner wall of the bore. Preferably, the bore includes a shoulder facing towards the first end, and the retainer contacts the shoulder. The suture loop passes through channels in an outer surface of the retainer.

These and other features and advantages of the present invention will be more fully appreciated with reference to the following detailed description which is to be read in conjunction with attached drawings.

BRIEF DESCRIPTION OF THE DRAWINGS

Like reference characters designate identical or corresponding components and units throughout the several views.

DETAILED DESCRIPTION OF THE PREFERRED EMBODIMENTS

Figure 1:
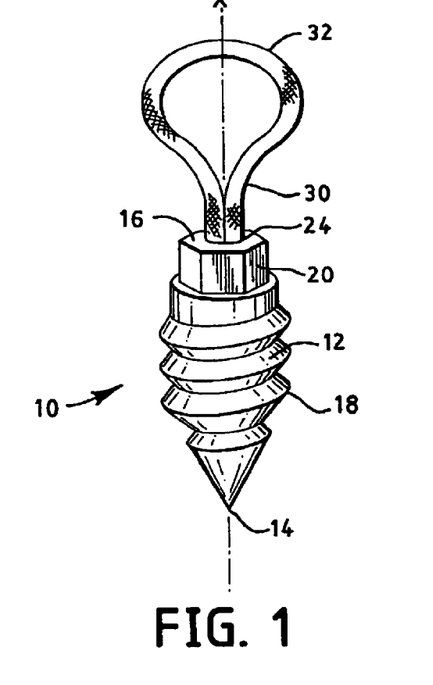
FIG. 1 is a perspective view of a suture anchor according to the present invention.
Figure 2:
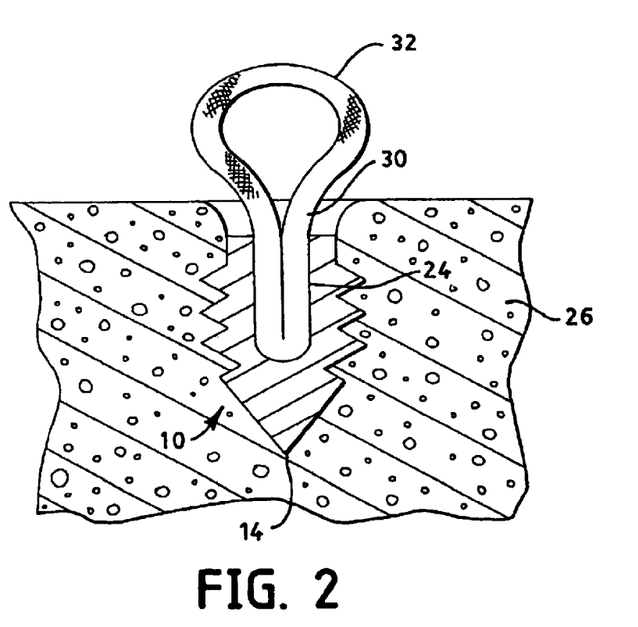
FIG. 2 is a sectional view of the suture anchor of FIG. 1 shown secured in a bone.

Suture anchors constructed in accordance with the present invention are primarily for use in orthopedic surgery for securing soft tissue to bone, though such anchors may be used in other fields as appropriate. As illustrated in FIG. 1, one suture anchor 10 includes an elongated body 12 which extends along a longitudinal axis X between a first end 14 and a second end 16. The elongated body 12 also includes an external threaded portion 18, and a drive head 20 at the second end 16. The elongated body 12 of FIGS. 1 and 2 also includes a bore 24 extending along the longitudinal axis X from the second end 16 towards the first end 14. FIG. 2 illustrates the anchor 10 received in bone 26.

As also shown in FIG. 2, the anchor 10 includes a continuous suture loop 30 secured within the bore 24 of the body 12 so that at least a portion of the loop 30 extends from the second end 16 of the body 12 to form an eyelet 32. In the embodiment of FIGS. 1 and 2, at least a portion of an outer surface of the suture loop 30 is bonded to an inner surface of the bore 24 of the body 12 to secure the suture loop 30 to the body 12.

If the suture loop 30 and the body 12 are made of a material amenable to bonding through the application of heat or energy thereto such as, for example, nylon (polyamide), polypropylene, Dacron® (polyester), polyglycolic acid (PGA), polyglyconate, and polydioxanone, the suture loop 30 and the body 12 are preferably ultrasonically bonded. Other suitable methods of bonding can be used if the suture loop 30 and the body 12 are made of another material, such as stainless steel, titanium, or some other durable, non-degradable, biocompatible material. The suture anchor 10 or parts thereof can be made of a bioresorbable material which will be resorbed after residing in a patient.

FIGS. 16 through 22 illustrate a method of forming a continuous suture loop 30 from a length of braided suture for use with the suture anchor of FIGS. 1 and 2. Alternatively, the suture anchor can incorporate a continuous, monofilamentous suture loop 30 having ends bonded using ultrasonic welding.

The external threaded portion 18 of the anchor 10 extends from the first end 14 in the embodiment shown. Also, the drive head 20 has a hexagonally shaped outwardly facing surface and can be mated with a external drive tool (not shown) with an inwardly facing hexagonally-shaped cavity for receiving the drive head 20. Various other means for cooperating with an external drive tool can alternatively be provided. The threads 18 of the threaded portion can be provided as self-tapping, and the anchor 10 can be provided with a self-drilling tip (not shown).

Figure 3:
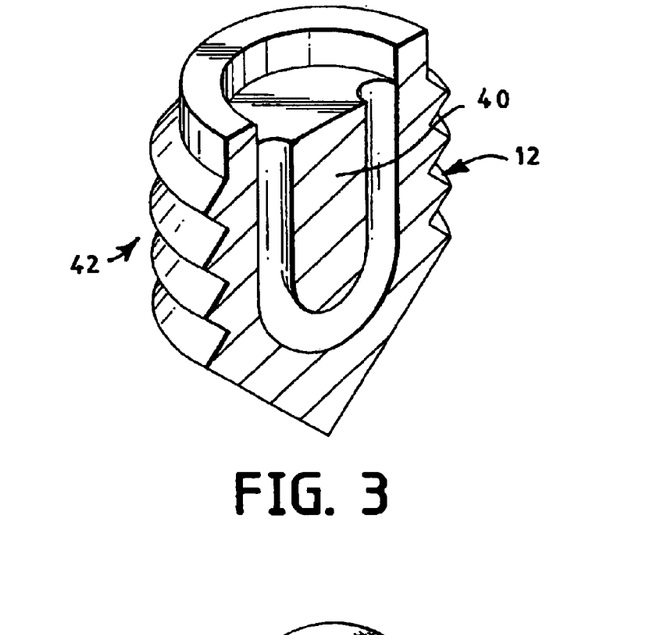
FIG. 3 is a perspective view of a portion of another suture anchor according to the present invention.
Figure 4:
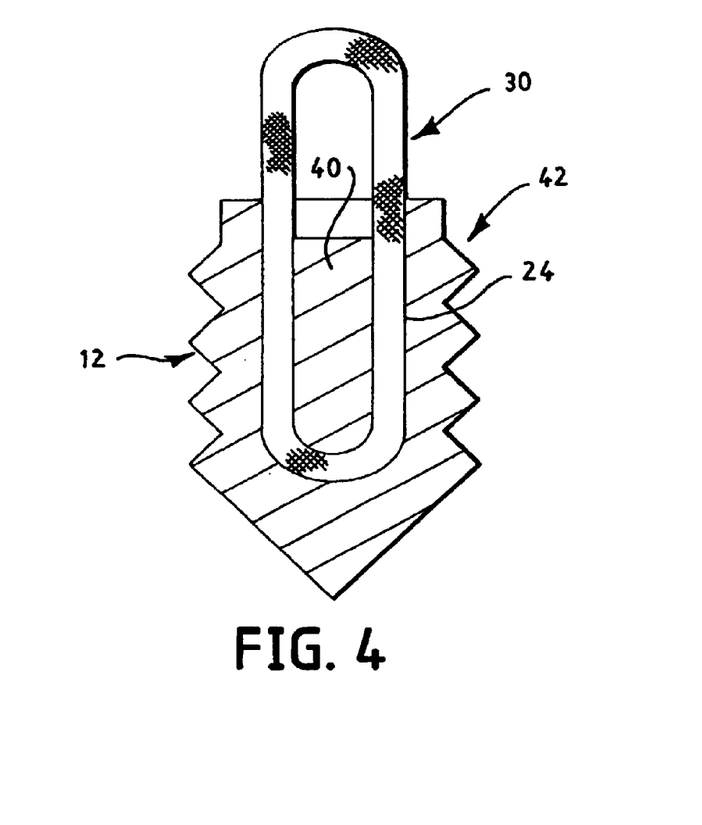
FIG. 4 is an elevation view of a continuous suture loop received within the portion of the suture anchor of FIG. 3.
Figure 5A:
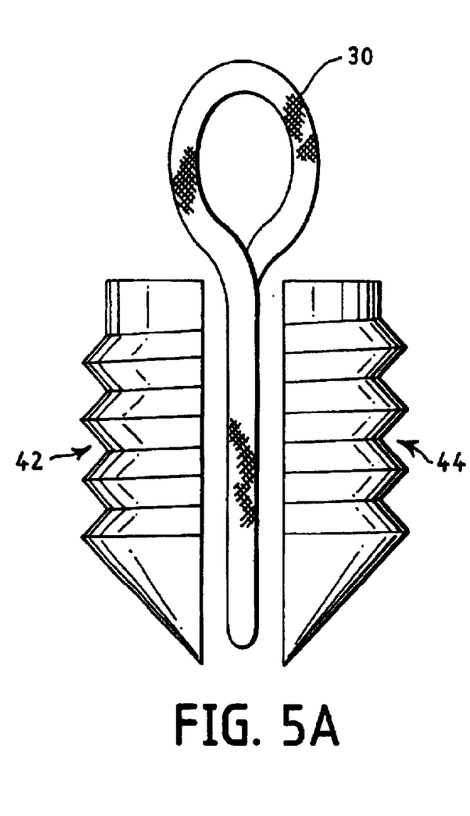
FIGS. 5A through 5C are side elevation views illustrating a method of assembling the suture anchor of FIG. 3.
Figure 5B:
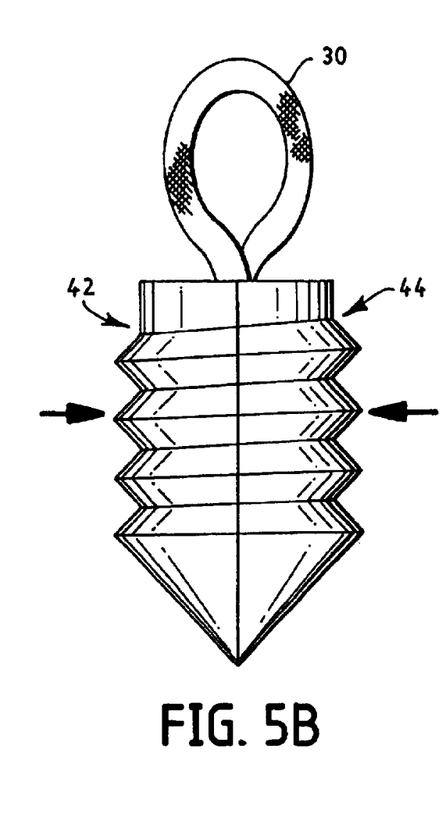
Figure 5C:
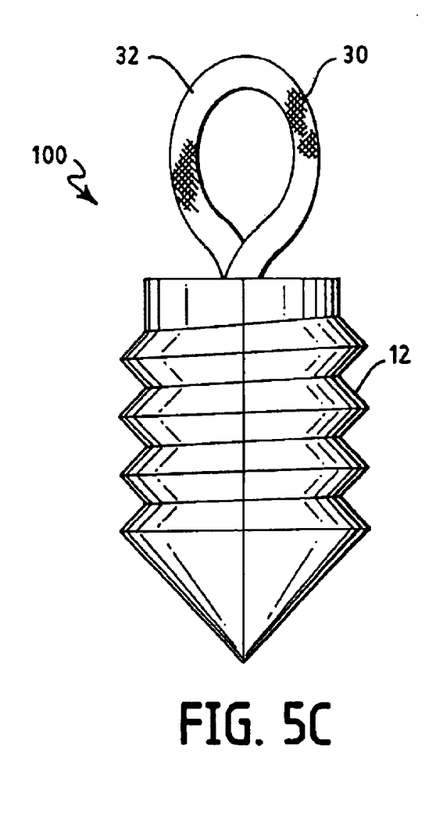

FIGS. 5A through 5C illustrate another embodiment of the present invention, wherein the suture loop 30 is secured to the body 12 of the suture anchor 100 with a retainer 40. The retainer 40 extends through the suture loop 30 generally laterally with respect to the axis X of the body 12, and is in turn secured to the body 12. As also shown in FIGS. 3 and 4, the retainer 40 is unitary with the body 12, and the body 12 and the retainer 40 are formed about the suture loop 30 from at least two longitudinal portions 42, 44 bonded together around the suture loop 30. Preferably, the two longitudinal portions are ultrasonically bonded to each other, but not to the suture loop 30, such that the loop 30 is movable between the retainer 40 and an inner surface of the bore 24. Since the suture loop 30 is not bonded to the body 12 or the anchor, there is a reduced chance of the suture being damaged, stressed and weakened during manufacturing.

Figure 6:
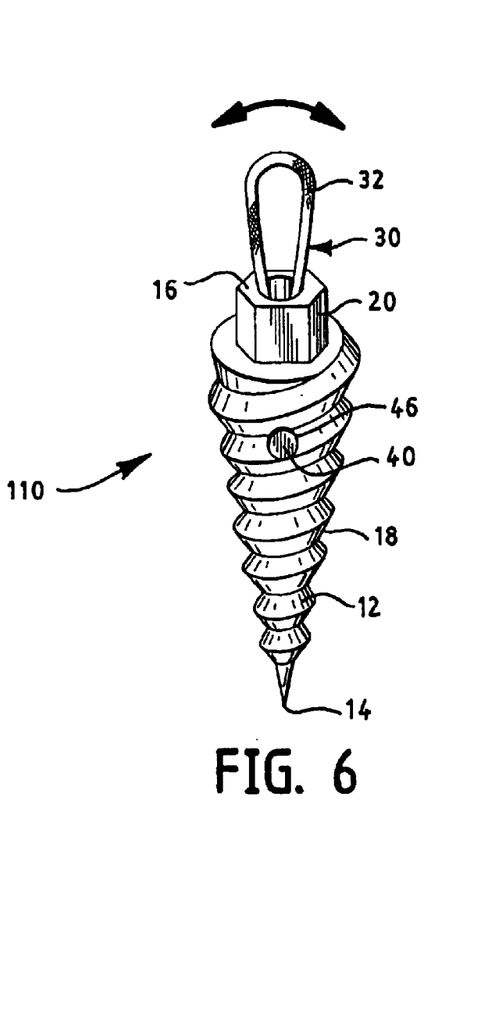
FIG. 6 is a perspective view of an additional suture anchor constructed in accordance with the present invention.
Figure 7:
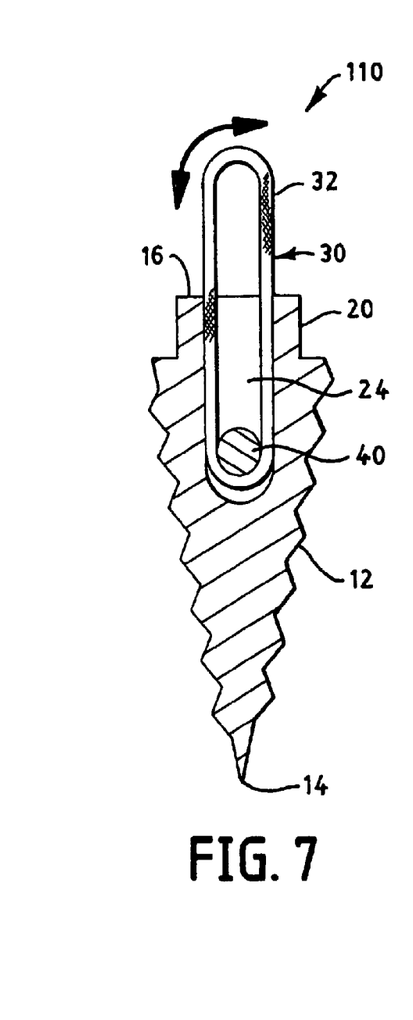
FIG. 7 is a sectional view of the suture anchor of FIG. 6.
Figure 8:
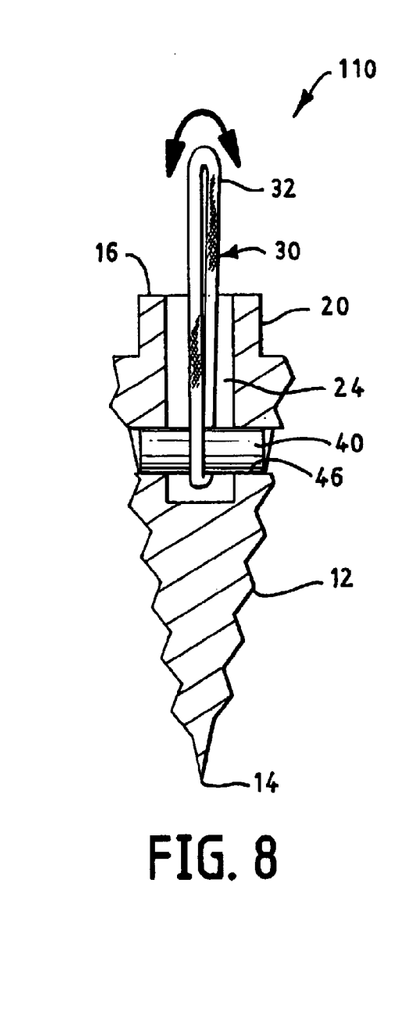
FIG. 8 is another sectional view of the suture anchor of FIG. 6.

In yet another embodiment, as shown in FIGS. 6 through 8, the suture anchor 110 includes a body 12 having a second bore 46 extending generally laterally with respect to the longitudinal axis X. The retainer 40 is received in the second bore 46, and at least a portion of an outer surface of the retainer 40 is secured to an inner surface of the second bore 46. The retainer 40 can be secured to the body 12 by a suitable means such as ultrasonic welding. Preferably, the suture loop 30 is not bonded to either of the body 12 or the retainer 40, such that the loop 30 is movable between the retainer 40 and the inner surface of the bore 24, in order to reduce stress on the suture loop 30.

Figure 9:
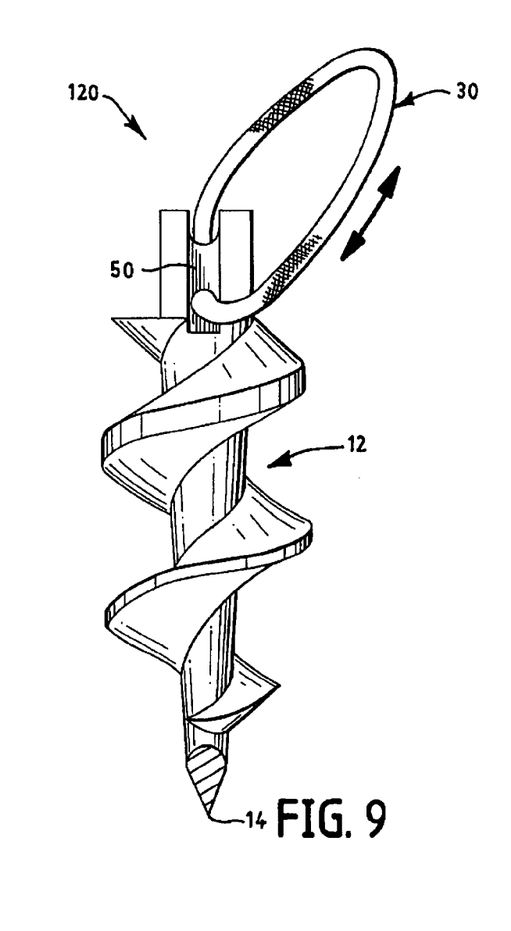
FIG. 9 is a side elevation view of a further suture anchor constructed in accordance with the present invention.
Figure 10:
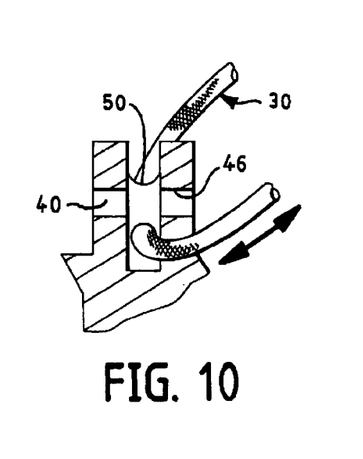
FIG. 10 is a sectional view of an end of the suture anchor of FIG. 9.
Figure 11:
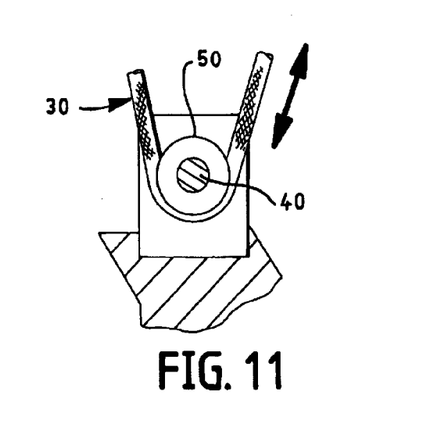
FIG. 11 is another sectional view of the end of the suture anchor of FIG. 9.

In the embodiment of FIGS. 9 through 11, the anchor 120 further includes a pulley 50 supporting the suture loop 30 on the retainer 40. Preferably, the suture loop 30 is not bonded to either of the body 12 or the pulley 50, such that the loop 30 is movable between the pulley 50 and the inner surface of the bore 24, in order to reduce stress on the suture loop 30. In addition, the pulley 50 is rotatably mounted on the retainer 40 to further reduce stress on the loop 30.

Figure 12:
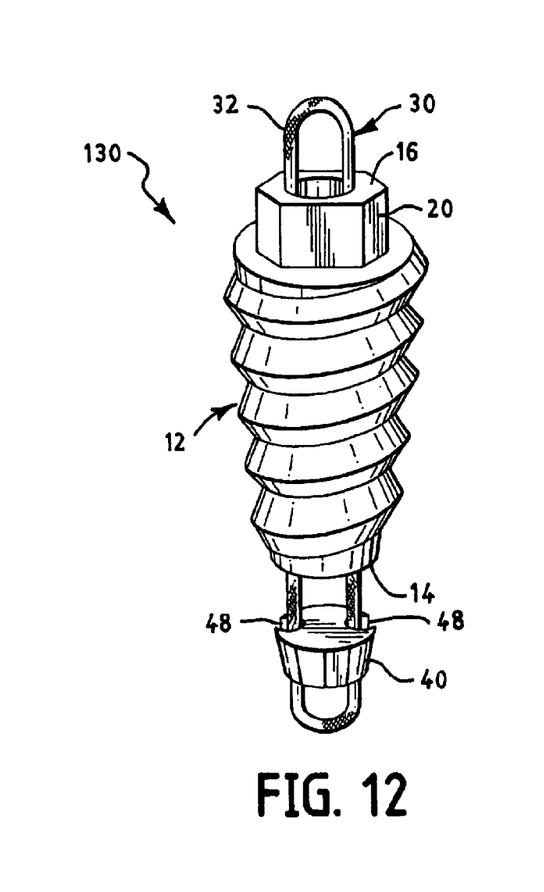
FIG. 12 is a perspective view of still another embodiment suture anchor constructed in accordance with the present invention.
Figure 13:
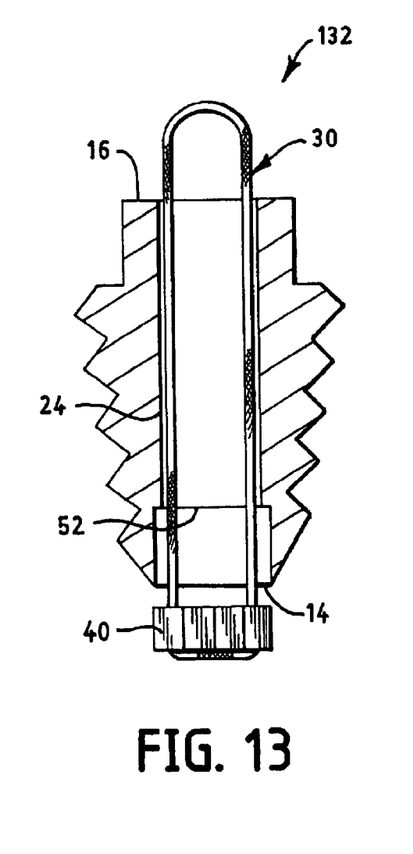
FIGS. 13 and 14 is a sectional view of the suture anchor of FIG. 10 illustrating a retainer and a continuous suture loop being secured in the anchor.
Figure 14:
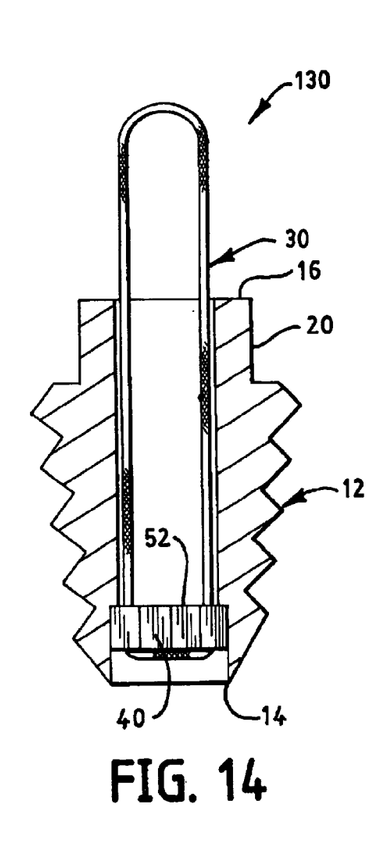
Figure 15:
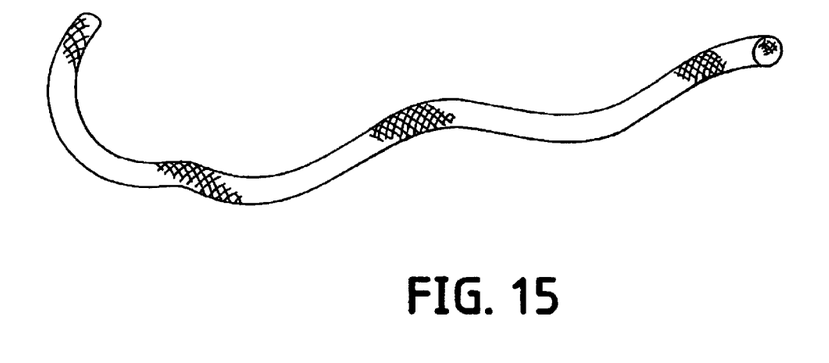
Figure 16:
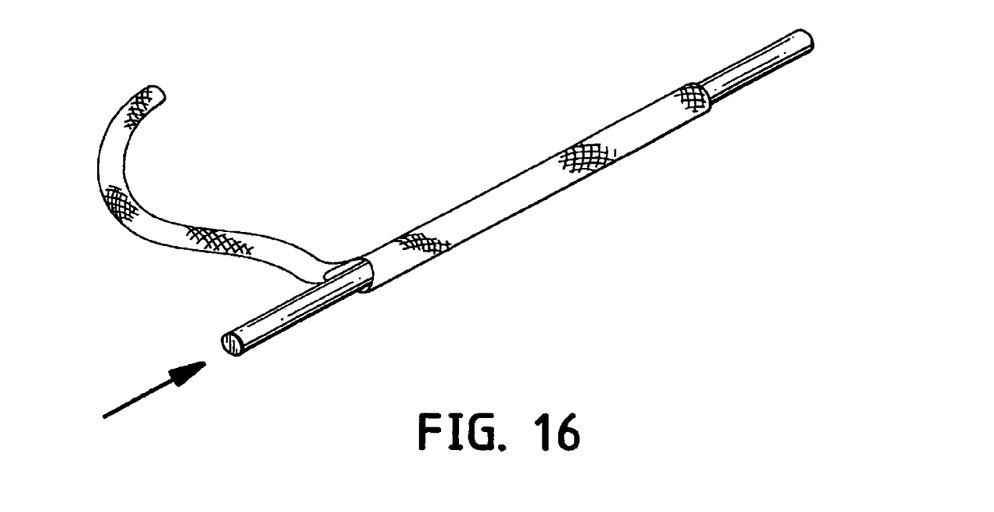
FIGS. 16 through 22 illustrate a method of forming a continuous suture ring from a length of braided suture.
Figure 17:
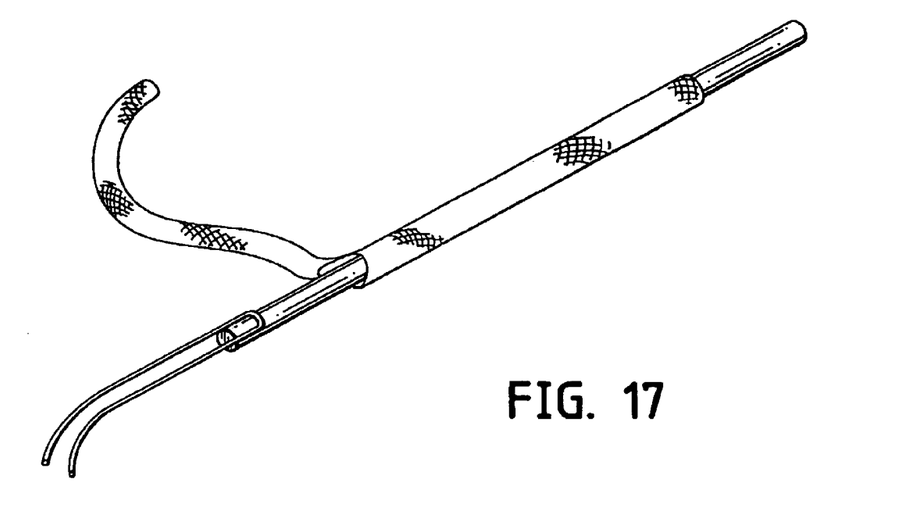
Figure 18:
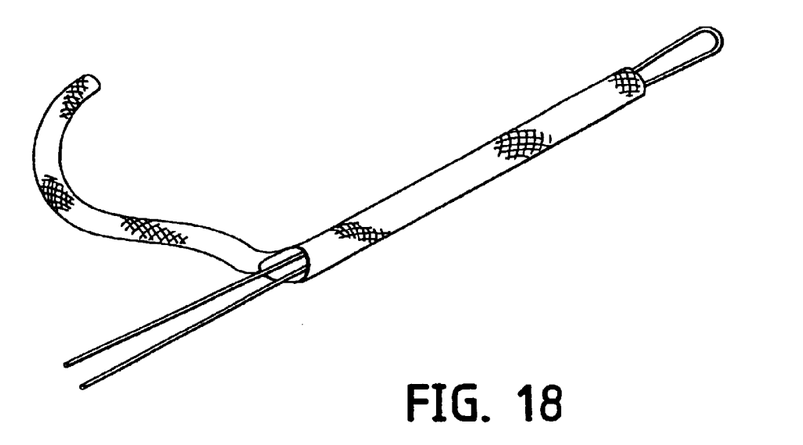
Figure 19:
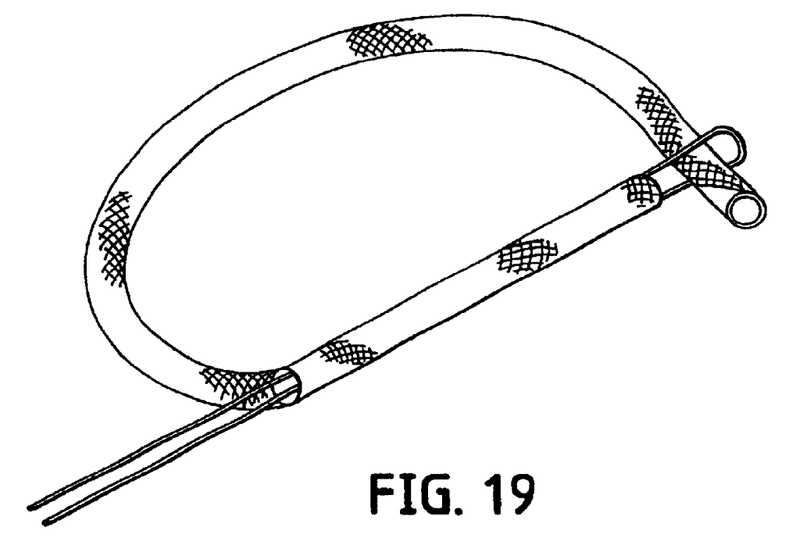
Figure 20:
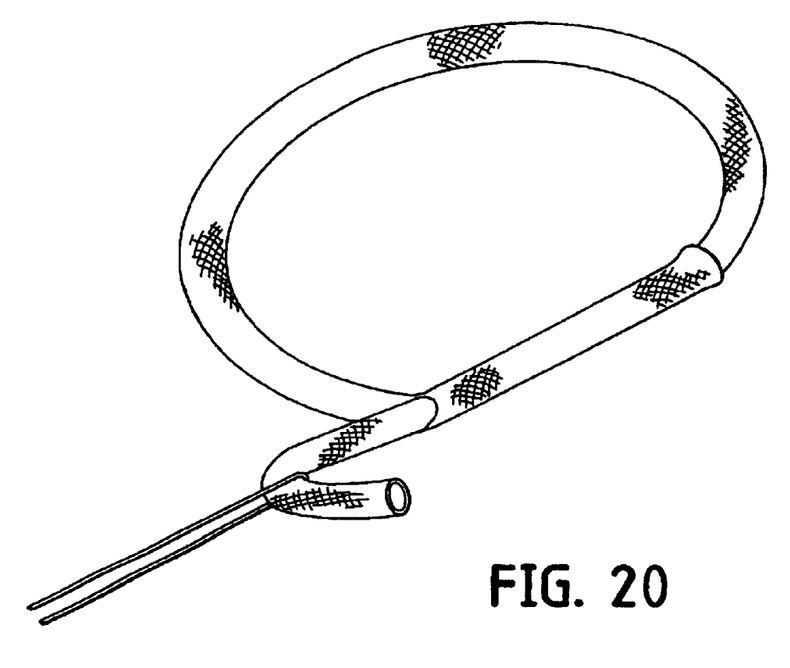
Figure 21:
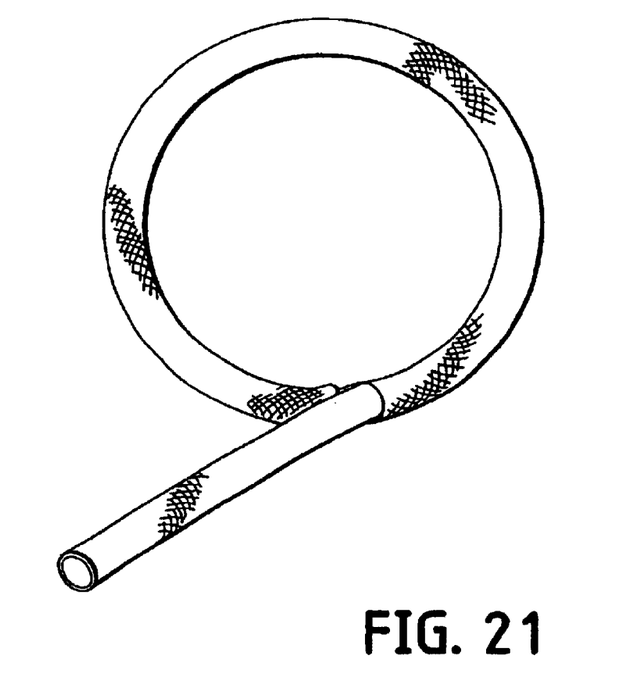
Figure 22:
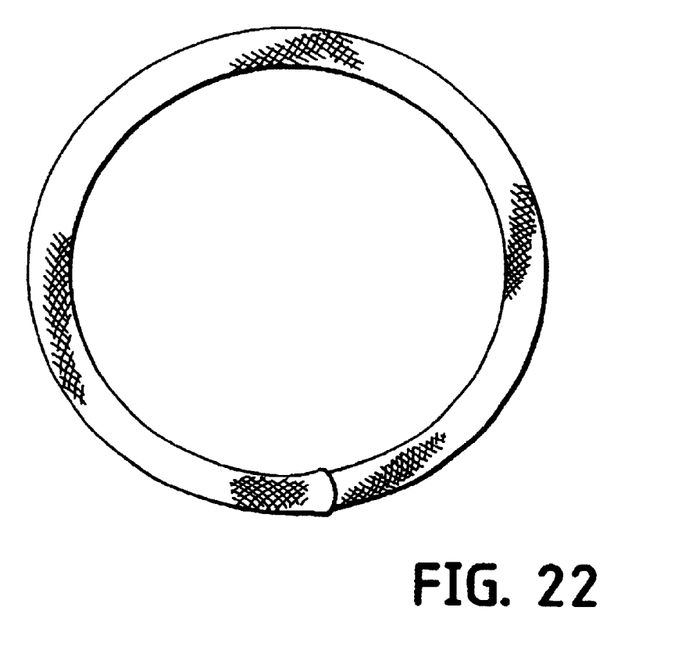

FIGS. 12 through 14 show a further embodiment, wherein the body 12 of the suture anchor 130 includes a longitudinal bore 24 that extends between the first and the second ends 14, 16 of the body 12, and the retainer 40 is wedged within an inner wall of the bore 24. Preferably, the bore 24 includes a shoulder 52 facing towards the first end 14, and the retainer 40 contacts the shoulder 52 to prevent further movement of the retainer 40. The retainer 40 can also be secured to the body 12 in a suitable manner, such as by bonding. The suture loop 30 passes through channels 48 in an outer surface of the retainer 40 in order to reduce stress on the suture loop 30.

It should be understood that the presently disclosed suture anchors may be embodied in other specific forms without departing from the spirit or essential characteristics thereof. The present embodiments are therefore to be considered in all respects as illustrative and not restrictive, the scope of the invention being indicated by the appended claims rather than by the foregoing description. All changes that come within the meaning and range of he equivalency of the claims are therefore intended to be embraced therein.

What is claimed is:

1. A suture anchor for securing soft tissue to bone, comprising:
    A) a rigid body extending along a longitudinal axis between opposing first and second ends, and having,
        an external threaded portion extending coaxially with the axis,
        a bore extending from the second end towards the first end; and
    B) a flexible eyelet fixedly attached to said body and formed by a continuous suture loop that has no knot and is secured within the bore of the body, wherein at least a portion of the loop extends from the second end of the body, and forms said flexible eyelet, and wherein the suture loop is captively held in the bore by a retainer secured to the body and traversing the bore and extending through the loop generally laterally with respect to the axis.

2. A suture anchor according to claim 1, wherein at least a portion of an outer surface of the suture loop is bonded to an inner surface of the bore of the body.

3. A suture anchor according to claim 1, wherein the loop is movable between the body and the retainer.

4. A suture anchor according to claim 1, wherein the retainer is unitary with the body.

5. A suture anchor according to claim 4, wherein the body and the retainer are formed about the suture loop from at least two longitudinal portions.

6. A suture anchor according to claim 5, wherein the longitudinal portions of the body are ultrasonically bonded.

7. A suture anchor according to claim 1, wherein the continuous suture loop is braided.

8. A suture anchor according to claim 1, wherein the body further includes a drive head at the second end.

9. A suture anchor according to claim 8, wherein the drive head has a hexagonal engagement surface facing laterally outwardly from the axis.

10. A mature anchor according to claim 1, wherein the external threaded portion includes a self-tapping threads.

11. A suture anchor according to claim 1, wherein the external threaded portion includes a self-drilling tip at the first end of the body.

12. A suture anchor according to claim 1, wherein the external threaded portion extends from the first end of the body.

13. A suture anchor according to claim 1, wherein said continuous suture loop has a substantially constant diameter.

14. A suture anchor according to claim 13, wherein at least a portion of an outer surface of the suture loop is bonded to an inner surface of the bore of the body.

15. A suture anchor according to claim 14, wherein the bore includes a shoulder facing towards the first end and the retainer contacts the shoulder.

16. A suture anchor according to claim 13, wherein the loop is movable between the body and the retainer.

17. A suture anchor according to claim 13, wherein the retainer is unitary with the body.

18. A suture anchor according to claim 17, wherein the body and the retainer are formed about the suture loop from at least two longitudinal portions.

19. A suture anchor according to claim 18, wherein the longitudinal portions of the body are ultrasonically bonded.

20. A suture anchor according to claim 13, wherein the continuous suture loop is braided.

21. A suture anchor according to claim 13, wherein the body further includes a drive head at the second end.

22. A suture anchor according to claim 21, wherein the drive head has a hexagonal engagement surface facing laterally outwardly from the axis.

23. A suture anchor according to claim 13, wherein the external threaded portion includes a self-tapping threads.

24. A suture anchor according to claim 13, wherein the external threaded portion includes a self-drilling tip at the first end of the body.

25. A suture anchor according to claim 13, wherein the external threaded portion extends from the first end of the body.

\* \* \* \* \*